United States Patent
Tuli

(10) Patent No.: US 12,329,615 B2
(45) Date of Patent: Jun. 17, 2025

(54) ABSORBENT ARTICLE WITH CONDUCTIVE MATERIAL ON TWO LAYERS

(71) Applicant: Raja Singh Tuli, Montreal (CA)

(72) Inventor: Raja Singh Tuli, Montreal (CA)

( * ) Notice: Subject to any disclaimer, the term of this patent is extended or adjusted under 35 U.S.C. 154(b) by 0 days.

(21) Appl. No.: 17/410,132

(22) Filed: Aug. 24, 2021

(65) Prior Publication Data

US 2022/0062066 A1    Mar. 3, 2022

Related U.S. Application Data

(60) Provisional application No. 63/071,066, filed on Aug. 27, 2020.

(51) Int. Cl.
*A61F 13/42*    (2006.01)
*A61F 13/512*    (2006.01)

(52) U.S. Cl.
CPC .......... *A61F 13/42* (2013.01); *A61F 13/5126* (2013.01); *A61F 2013/424* (2013.01)

(58) Field of Classification Search
CPC .................. A61F 13/42; A61F 13/5126; A61F 2013/424; A61F 2013/425; A61F 2013/428
See application file for complete search history.

(56) References Cited

U.S. PATENT DOCUMENTS

| | | | | |
|---|---|---|---|---|
| 5,760,694 | A * | 6/1998 | Nissim | A61F 13/42 128/885 |
| 10,561,541 | B1 * | 2/2020 | Heyl | A61F 13/42 |
| 2013/0324955 | A1 * | 12/2013 | Wong | A61F 13/42 604/361 |
| 2016/0166438 | A1 * | 6/2016 | Rovaniemi | A61F 13/42 493/320 |
| 2017/0071797 | A1 * | 3/2017 | Wu | A61F 13/141 |
| 2018/0333306 | A1 * | 11/2018 | Ahong | A61B 5/6843 |

OTHER PUBLICATIONS

Apply Definition & Meaning, Merriam-Webster, https://www.merriam-webster.com/dictionary/apply (Year: 2024).*
Impregnate Definition & Meaning, Merriam-Webster, https://www.merriam-webster.com/dictionary/impregnate (Year: 2024).*

* cited by examiner

*Primary Examiner* — Susan S Su
*Assistant Examiner* — Katherine-Ph Minh Pham

(57) ABSTRACT

An absorbent article is provided herein that comprises a first layer with at least two conductive lines being provided thereon along and throughout its length, and a second porous layer overlaying the first layer. Conductive material is applied onto the second porous layer such that the conductive material impregnated into the second porous layer connects the conductive material on the top surface of the second porous layer to the conductive lines on the first layer.

6 Claims, 5 Drawing Sheets

ABSORBENT ARTICLE WITH CONDUCTIVE MATERIAL ON TWO LAYERS

CROSS-REFERENCE TO RELATED APPLICATIONS

This application claims priority to U.S. provisional patent application No. 63/071,066, entitled "ABSORBENT ARTICLE WITH CONDUCTIVE MATERIAL ON TWO LAYERS," filed on Aug. 27, 2020. The content of this U.S. provisional patent application is hereby incorporated by reference in its entirety for all purposes.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Field of the Invention

The present disclosure generally relates to absorbent article, and specifically to absorbent article with wetness detection means.

Description of Related Art

Disposable absorbent article such as disposable diaper is a product that is capable of receiving and retaining bodily exudates or excretions so as to prevent contamination of the clothing or external environment. As an example, with a disposable diaper, the user is allowed to urinate or defecate without the use of a toilet. In addition to diapers, there are numerous other types of disposable absorbent articles such as e.g. under pads, incontinence pads, fitted briefs, belted shields, liners, all-in-one pads, pull-up incontinence pants, training pants, protective underwear, catamenial napkins, and incontinence guards etc. It is to be understood that the list of disposable absorbent articles identified above is not exhaustive and that these and other absorbent articles can be used with the present disclosure and are within the scope of the present disclosure. It is also to be understood that a reference in this specification to any one such article, such as a "diaper" is to be taken to be a reference to any and all other suitable absorbent articles including incontinence garments, pads and the like.

In order to prevent contamination of the clothing or external environment, disposable absorbent article is provided with an absorbent core capable of receiving and retaining bodily exudates or excretions, and a substantially liquid impervious layer. In general, disposable absorbent products consist of a layered construction, which allows the bodily exudates or excretions to be distributed and transferred to the absorbent core where they are retained in. In everyday use, a disposable absorbent article may be used until the absorbent core is saturated with e.g. bodily exudates or excretions. When the absorbent core is saturated, the disposable absorbent article needs to be removed, disposed of, and replaced with a clean and dry article.

In order for wetness detection, the existing art relies in general on the capacitive coupling between the sensing electrodes embedded in an absorbent article and an external alerting device. As an example, WO2021/087600A1 discloses the capacitive coupling between a pod and the sensor lines in a diaper. However, it is appreciated that compared with a direct physical contact, the capacitive coupling is more prone to a poor engagement.

Thus, it is desirable to provide absorbent articles, and systems that enable wetness detection with direct physical contact.

BRIEF SUMMARY OF THE INVENTION

Embodiments are presented herein of, inter alia, absorbent articles, and systems for detecting the presence and/or amount of wetness (e.g. the exudates or excretions) in the absorbent article with direct physical contact.

In an embodiment of the present disclosure, an absorbent article is provided that comprises: a first layer with at least two conductive lines being provided thereon along and throughout its length, and a second porous layer overlaying the first layer. In the embodiment, conductive material is applied onto the second porous layer such that the conductive material impregnated into the second porous layer connects the conductive material on the top surface of the second porous layer to the conductive lines on the first layer.

This summary is intended to provide a brief overview of some of the subject matter described in this document. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

BRIEF DESCRIPTION OF THE DRAWINGS

The various preferred embodiments of the present invention described herein can be better understood by those skilled in the art when the following detailed description is read with reference to the accompanying drawings. The components in the figures are not necessarily drawn to scale and any reference numeral identifying an element in one drawing will represent the same element throughout the drawings. The figures of the drawing are briefly described as follows.

Figure 1:
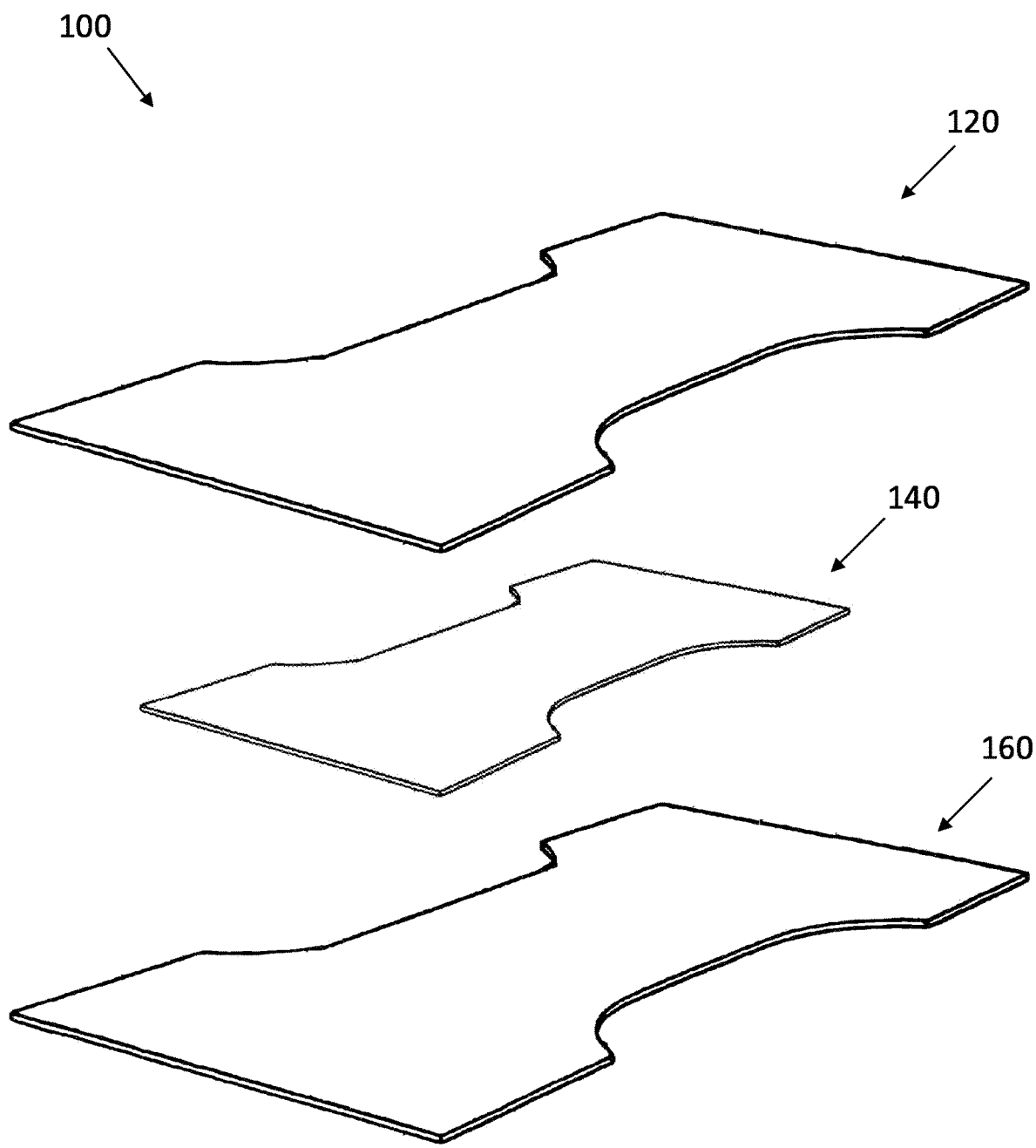
FIG. 1 illustrates an exemplary disposable absorbent article in an exploded perspective view.

While the features described herein are susceptible to various modifications and alternative forms, specific embodiments thereof are shown by way of example in the drawings and are herein described in detail. It should be understood, however, that the drawings and detailed description thereto are not intended to be limiting to the particular form disclosed, but on the contrary, the intention is to cover all modifications, equivalents and alternatives falling within the spirit and scope of the subject matter as defined by the appended claims.

DETAILED DESCRIPTION OF THE INVENTION

FIG. 1 illustrates an exemplary disposable absorbent article in an exploded perspective view. As illustrated, a disposable absorbent article 100 primarily consists of an absorbent core 140 sandwiched between a liquid pervious layer 120 and a substantially liquid impervious layer 160.

As illustrated in the exemplary diaper of FIG. 1, a disposable absorbent article 100 has a substantially liquid impervious layer 160 configured to prevent the bodily exudates or excretions absorbed and retained in the absorbent core 140 from wetting articles, such as bed sheets and undergarments, which contact the disposable absorbent article 100. On top of the layer 160 is disposed an absorbent core 140 made of a superabsorbent material. On top of the absorbent core 140 is a liquid pervious layer 120 that is joined to the layer 160 in an assembled state of the disposable absorbent article and is placed next to the skin of the user when in use. Additional structural features such as additional layer(s), elastic members and fastening means for securing the article in place, such as tape tab fasteners, may also be included.

The liquid pervious layer 120 is configured to be penetrable by bodily exudates and excretions in a direction into the absorbent core 140 to enable them to be absorbed and retained in the underlying absorbent core 140. It is appreciated that the layer 120 may be made of a variety of liquid pervious materials, e.g. nonwoven fabric.

The absorbent core 140 is made up of hydrophilic superabsorbent polymers (SAP) and fibrous material, as a non-limiting example. The polymers act like tiny sponges that retain many times their weight in liquid.

The substantially liquid impervious layer 160 is made of a material substantially impervious to liquids. As an example, the substantially liquid impervious layer 160 may be manufactured from a thin plastic film, although other liquid impervious materials may also be used. As described above, the substantially liquid impervious layer 160 is configured to prevent the bodily exudates or excretions absorbed and retained in the absorbent core from wetting articles, such as bed sheets and undergarments, which contact the diaper.

As illustrated in the exemplary diaper of FIG. 1, the layers 120 and 160 are coextensive and have generally larger dimension, in length and/or width, than the absorbent core 140.

Figure 2:
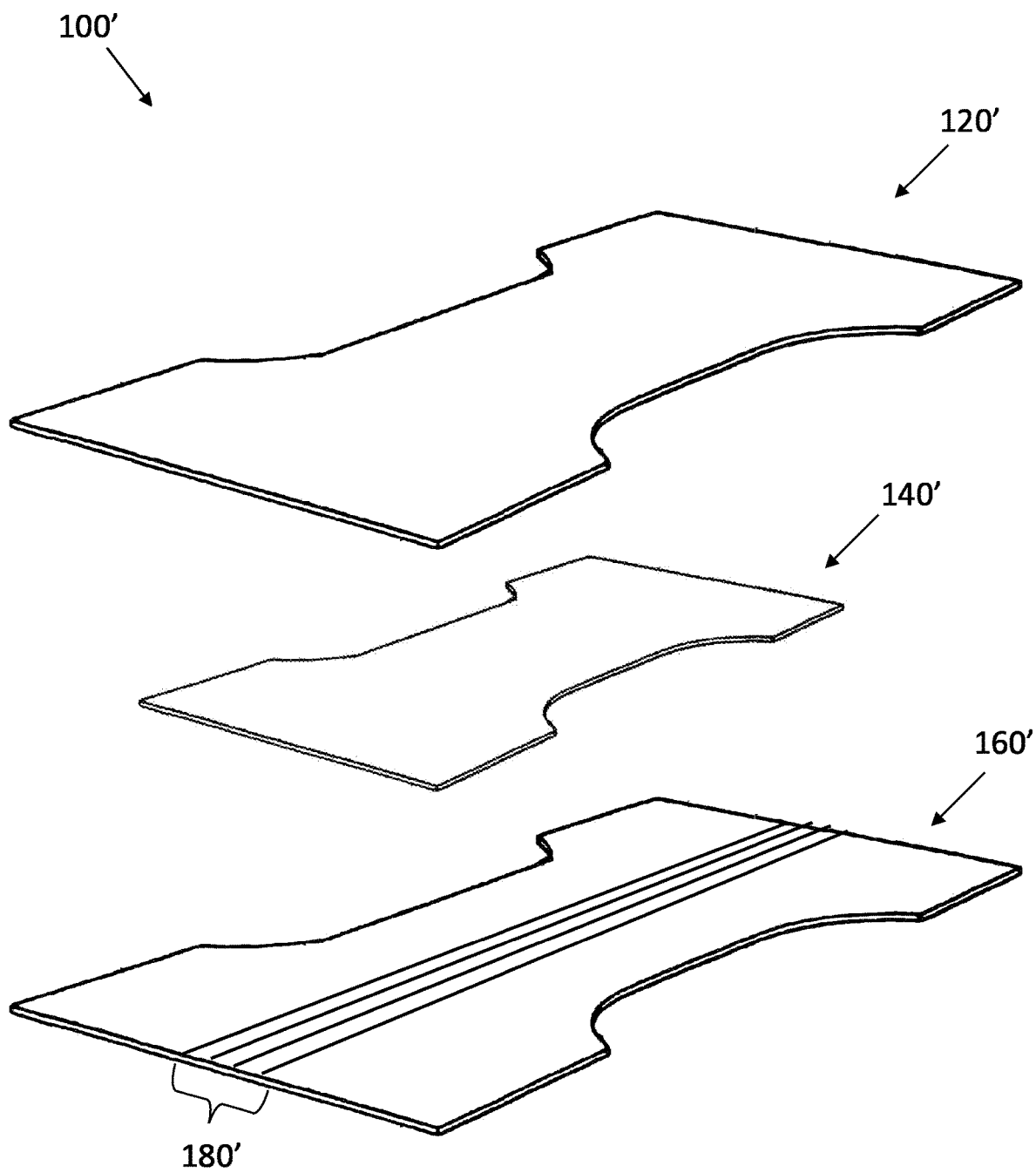
FIG. 2 illustrates an exemplary disposable absorbent article with four spaced-apart conductive lines being provided on the top side of its substantially liquid impervious layer, according to an embodiment of the present disclosure.

In order to detect the presence and/or amount of wetness (e.g. the bodily exudates or excretions) in a disposable absorbent article, in particular in its absorbent core, a number of (e.g. at least two) spaced-apart conductive lines are provided on the top side (i.e. the side facing the absorbent core) of the substantially liquid impervious layer along the length of the disposable absorbent article, in an embodiment of the present disclosure. In FIG. 2, an exemplary disposable absorbent article 100' is depicted with four spaced-apart conductive lines 180' being provided on the top side of the substantially liquid impervious layer 160', as an example. The spaced-apart conductive lines 180' in the disposable absorbent article 100' operate in cooperation with a pod 200 (to be described below in reference to FIG. 3), to detect the presence and/or amount of the exudates or excretions in the disposable absorbent article 100'.

It is to be noted that the spaced-apart conductive lines (e.g. 180') may be provided on any layer, e.g. another layer underneath the absorbent core, in a disposable absorbent article, provided that they can operate in a similar way to those on the substantially liquid impervious layer, that is, provided that the spaced-apart conductive lines can operate in cooperation with a pod (to be described below) to detect the presence and/or amount of the exudates or excretions in the disposable absorbent article.

Figure 3:
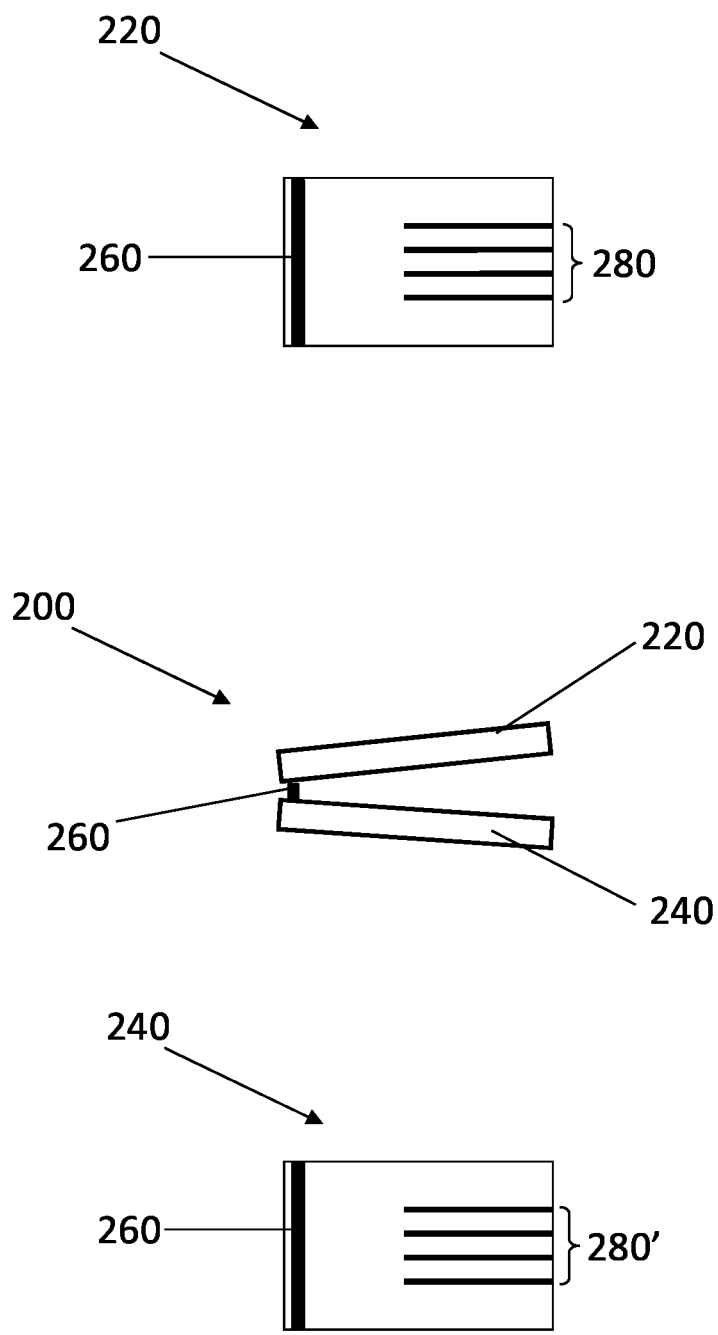
FIG. 3 illustrates an exemplary pod that can be used with an absorbent article with conductive lines to detect the presence and/or amount of wetness (e.g. the exudates or excretions) in the absorbent article, according to an embodiment of the present disclosure.

As illustrated in FIG. 3, an exemplary pod 200 primarily consists of two halves 220 and 240 that are pivotably coupled to each other with a pivotal connection 260. At least one of the two halves 220 and 240 is provided with a number of (e.g. at least two) contacts 280 or 280' on its inner side (i.e. the side facing the other half). As a non-limiting example, both the two halves 220 and 240 have each a number of contacts 280 or 280' on their respective inner side, as illustrated in FIG. 3. In the example as illustrated in FIG. 3, there are four (the same number as the conductive lines 180' as illustrated in FIG. 2) contacts 280 and 280' on the two halves 220 and 240 respectively.

In operation, the pod 200 as illustrated in FIG. 3 is clipped on a disposable absorbent article (e.g. 100' as illustrated in FIG. 2) at one of its waist end edges and coupled to the conductive lines (e.g. 180' in FIG. 2) with the contacts 280 and/or 280' on the pod 200. In use, the bodily exudates or excretions absorbed and retained in the absorbent core (e.g. 140' in FIG. 2) of the absorbent article will cause at least two of the spaced-apart conductive lines (e.g. 180' in FIG. 2) to be connected to each other, and thus the pod 200 can detect the presence and/or amount of the exudates or excretions in the disposal absorbent article (e.g. 100' in FIG. 2) by applying a voltage across the corresponding conductive lines (e.g. 180' in FIG. 2) with the contacts 280 or 280' and measuring the current.

As mentioned above, in a disposable absorbent article the spaced-apart conductive lines may be provided on any layer, on which at least two of the spaced-apart conductive lines, with the aid of the bodily exudates or excretion absorbed and retained in the disposable absorbent article, will connect to each other, which in turn enables the detection of the presence and/or amount of the exudates or excretions in the disposal absorbent article.

It is to be noted that the pod 200, in particular its contacts 280 and 280', cannot make physical contact with the conductive lines (e.g. 180' in FIG. 2) on the disposable absorbent article (e.g. 100' in FIG. 2) due to the presence of outermore material or layer(s) of the article, e.g. material or layer(s) further away from the absorbent core, with respect to the conductive lines, e.g. the substantially liquid impervious layer (e.g. 160' in FIG. 2) and/or the liquid pervious layer (e.g. 120' in FIG. 2). That is, in use, the pod 200 is capacitively coupled to the conductive lines (e.g. 180' in FIG. 2) by aligning its contacts 280 and 280' with the conductive lines (e.g. 180' in FIG. 2) and placing them in close proximity. However, it is appreciated by those skilled in the art that compared with a direct physical contact, the capacitive coupling is more prone to a poor engagement.

In an embodiment of the present disclosure, in addition to providing at least two conductive lines (e.g. four conductive lines) on the top side (i.e. the side facing the absorbent core) of a layer underneath the absorbent core e.g. the substantially liquid impervious layer, the same number of conductive lines in the same arrangement are provided on the top side (i.e. the side facing the skin of the user) of the liquid pervious layer, opposite to those provided on e.g. the substantially liquid impervious layer, in order to enable a direct physical contact between the contacts (e.g. 280 and/or 280') on the pod (e.g. 200 in FIG. 2) and the conductive lines on the layer underneath the absorbent core in the absorbent article (to be described below).

It is to be noted that the same number of conductive lines may be provided on any porous layer in the absorbent article, e.g. on another porous layer above the absorbent core, provided that they enable a direct physical contact between the contacts on the pod and the conductive lines in the absorbent article. It is also to be noted that the same number of conductive lines may be provided on either or both of the top and bottom sides of that porous layer, because such layer is so porous that both its bottom and top sides will be impregnant with the conductive material.

Figure 4:
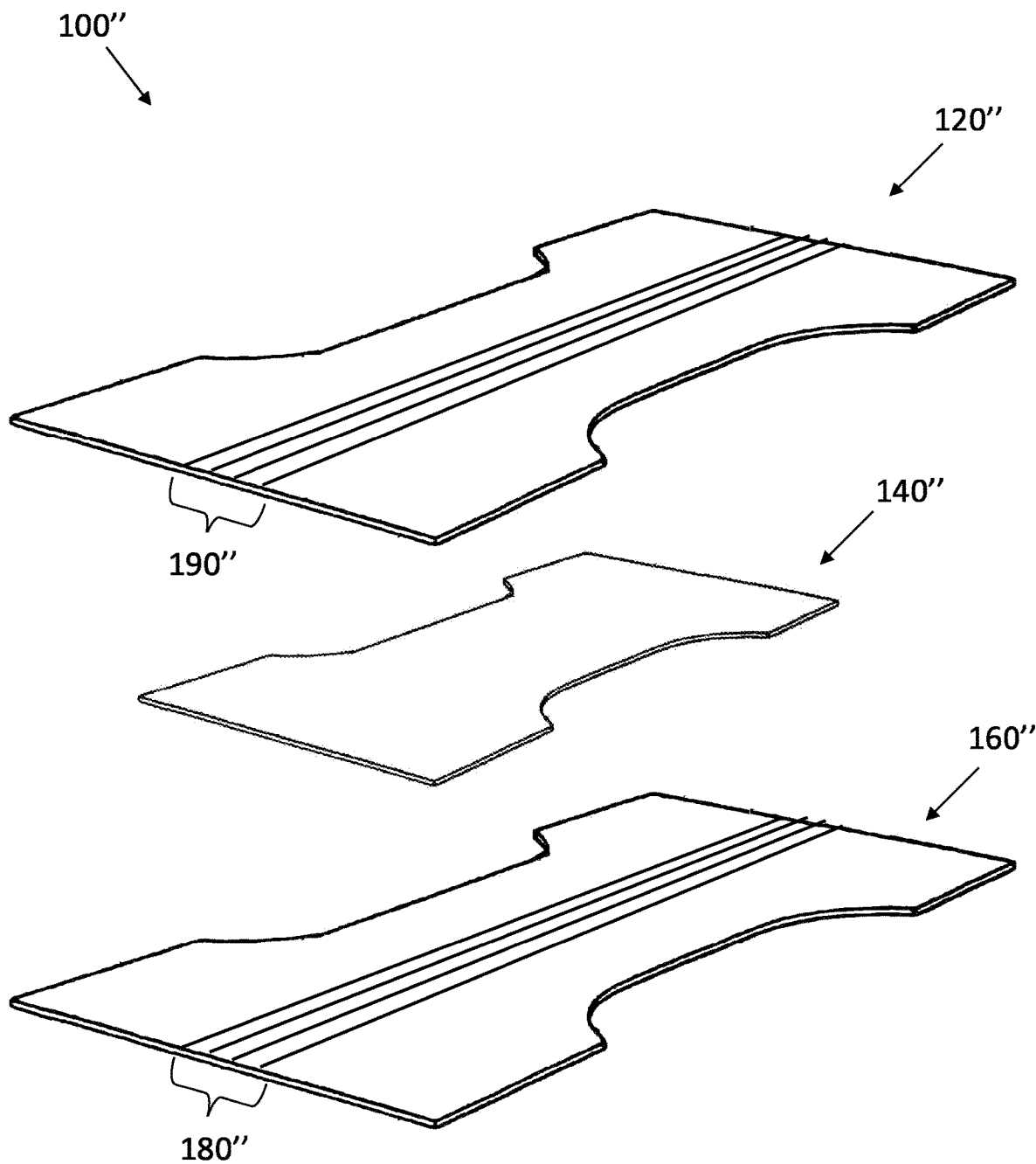
FIG. 4 illustrates an exemplary absorbent article that enable a direct physical contact with contacts on a pod, according to an embodiment of the present disclosure.

An exemplary absorbent article 100" according to this embodiment is illustrated in FIG. 4. Similarly to the absorbent article 100' as illustrated in FIG. 2, the exemplary absorbent article 100" as illustrated in FIG. 4 primarily consists of a liquid pervious layer 120", an absorbent core 140" and a substantially liquid impervious layer 160" in a layered construction. The absorbent article 100" differs from the absorbent article 100' in that the same number of conductive lines 190" are provided in the same arrangement on the top side of the liquid pervious layer 120", as those conductive lines 180' on the substantially liquid impervious layer 160". In the assembled state of the absorbent article 100", the conductive lines 190" overlap and are opposite to the conductive lines 180".

Figure 5:
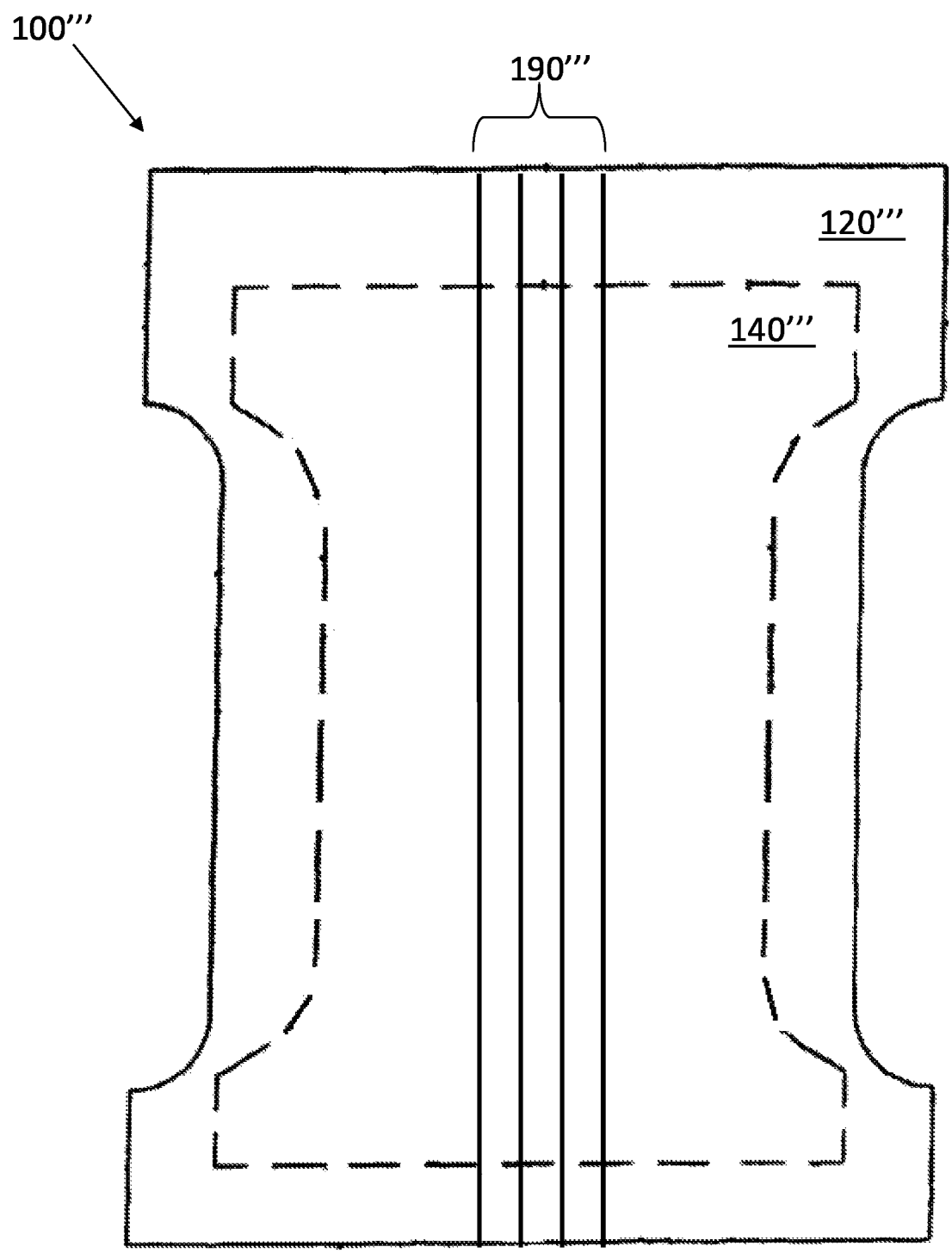
FIG. 5 is a plan view of an exemplary absorbent article in an assembled, but flat-out and uncontracted state, according to an embodiment of the present disclosure.

In the assembled state of a disposable absorbent article e.g. diaper, the liquid pervious layer and the substantially liquid impervious layer are joined together with the absorbent core being sandwiched therebetween. FIG. 5 is a plan view of an exemplary absorbent article 100''' according to an embodiment of the present disclosure, showing the exemplary absorbent article 100''' in its assembled, but flat-out and uncontracted state.

As mentioned above, an absorbent article is manufacture by joining a liquid pervious layer and a substantially liquid impervious layer of the substantially same dimension together, with an absorbent core being sandwiched therebetween. As illustrated in the plan view in FIG. 5, in the exemplary absorbent article 100''' a liquid pervious layer 120''' is jointed to a substantially liquid impervious layer that is overlapped and hidden from view by the liquid pervious layer 120''' and thus cannot be seen in FIG. 5. An absorbent core 140''' of a smaller dimension is sandwiched between the liquid pervious layer 120''' and the substantially liquid impervious layer, that is, in the plan view as illustrated in FIG. 5, the absorbent core 140''' is positioned underneath the liquid pervious layer 120''' and hidden from view by it and thus is depicted with dashed lines. In the exemplary absorbent article 100''', a plurality of (e.g. 4, as illustrated in FIG. 5) spaced-apart conductive lines 190''' are provided (e.g. printed) on the top side of the liquid pervious layer 120'''. As described above in reference to FIG. 4, the same number of (e.g. 4, in the exemplary embodiment as illustrated in FIG. 5) spaced-apart conductive lines in the same arrangement are provided (e.g. printed) on the top side of the substantially liquid impervious layer, which is overlapped and hidden from view by the conductive lines 190''' and thus cannot be seen in FIG. 5.

It is also appreciated that the liquid pervious layer and the substantially liquid impervious layer are joined together around their peripheries (i.e. the outer edges that do not contact with the absorbent core), which makes some of the fibers of the liquid pervious layer and the substantially liquid impervious layer in these areas connected or contacted. And, when being clipped on an absorbent diaper at its waist end edge, a pod will further make some of the fibers of the liquid pervious layer and the substantially liquid impervious layer in this waist end edge contact.

It is further appreciated that in order to enable the bodily exudates and excretions to penetrate into the absorbent core, the liquid pervious layer of a disposable absorbent article is made to be very porous. Because of the porousness of the liquid pervious layer (e.g. 120" and 120''' in the example as illustrated in FIGS. 4 and 5), when the conductive lines (e.g. 190" and 190''' in FIGS. 4 and 5) are provided (e.g. printed) on the liquid pervious layer (e.g. 120" and 120''' in FIGS. 4 and 5), the conductive material, e.g. carbon ink, gets impregnated all the way through the liquid pervious layer (e.g. 120" and 120''' in FIGS. 4 and 5).

It is to be understood that, when the peripheries of the liquid pervious layer (e.g. 120" and 120''' in FIGS. 4 and 5) and the substantially liquid impervious layer (e.g. 160" in FIG. 4) are compressed and/or joined together, some of the fibers of the liquid pervious layer (e.g. 120" and 120''' in FIGS. 4 and 5) in its periphery that are impregnated with the conductive material e.g. carbon ink will connect the conductive lines (e.g. 190" and 190''' in FIGS. 4 and 5) on the liquid pervious layer (e.g. 120" and 120''' in FIGS. 4 and 5) to the conductive lines (e.g. 180" in FIG. 4) on the substantially liquid impervious layer (e.g. 160" in FIG. 4), which in turn enables the direct physical contact of the conductive lines (e.g. 180" in FIG. 4) on the substantially liquid impervious layer (e.g. 160" in FIG. 4) with the contacts (e.g. 280 or 280' in FIG. 3) of the pod (e.g. 200 in FIG. 3) and thus enable the detection of the wetness in the absorbent article with direct contact.

It is to be noted that, one possible issue with providing conductive lines on the liquid pervious layer is that the printing on such layer is not as good as on other media because it is very porous, like fibrous material, so it may not make full contact everywhere. However, as long as the conductive material e.g. carbon ink is provided (e.g. printed) on the liquid pervious layer, at least some of its fibers will be impregnated with conductive material e.g. carbon ink and thus will make contact. Therefore, it provides a contact to enable the wetness to be determined.

It is to be noted that the conductive lines on the porous layer do not have to be continuous, e.g. do not have to be electrically conductively continuous. Alternatively, in another embodiment of the present disclosure, the conductive lines on the porous layer are not continuous. For example, little circles or spots or any other shape (instead of continuous lines) are provided (e.g. printed) on the liquid pervious layer with the conductive material. That is, conductive lines (e.g. two or four conductive lines) are provided (e.g. printed) on the substantially liquid impervious layer while e.g. little conductive circles or spots are provided (e.g. printed) on the liquid pervious layer.

It is contemplated that, the conductive lines and/or the little conductive circles or spots can be provided (e.g. printed) on the porous layer e.g. the liquid pervious layer throughout the length of the absorbent article or only in the waist end periphery where the pod is expected to be clipped on.

Those skilled in the art will appreciate that, the teaching of the present disclosure is not necessarily limited to the liquid pervious layer and the substantially liquid impervious layer of a disposable absorbent article. Instead, it may involve any two layers in a disposable absorbent article, where the purpose of the lower layer is the detection of the wetness (e.g. bodily exudates or excretions) and/or its amount and the detection of wetness and/or its amount is done by at least two conductive lines on that lower layer that are connected due to the wetness, while the higher layer is used to connect for the purpose of pod, i.e. to make physical contact with the lower layer.

Although the embodiments above have been described in considerable detail, numerous variations and modifications will become apparent to those skilled in the art once the above disclosure is fully appreciated. It is intended that the following claims be interpreted to embrace all such variations and modifications.

The invention claimed is:

1. An absorbent article, comprising:
   a first layer with at least two conductive lines being provided thereon along and throughout its length, the at least two conductive lines being configured to detect the presence and/or amount of wetness in the absorbent article; and
   a second porous layer overlaying the first layer;
   wherein conductive material is applied onto the second porous layer to provide on the second porous layer a same number of conductive lines in a same arrangement as those provided on the first layer such that the conductive lines provided on the second porous layer overlap and are opposite to those provided on the first layer, and those of the conductive material that are impregnated into the second porous layer connects the conductive lines provided on the second porous layer to the conductive lines on the first layer, thereby enabling a direct contact between the at least two conductive lines on the first layer of the absorbent article and contacts of a pod clipped on the absorbent article.

2. The absorbent article as claimed in claim 1, wherein the conductive lines provided on the second porous layer is made up of conductive patterns.

3. The absorbent article as claimed in claim 2, wherein the conductive patterns are provided throughout the second porous layer.

4. The absorbent article as claimed in claim 2, wherein the conductive patterns are provided in the end area of the second porous layer where a pod is expected to clip.

5. The absorbent article as claimed in claim 2, wherein the conductive patterns are circles or spots.

6. The absorbent article as claimed in claim 1, further comprising an absorbent core sandwiched between the first layer and the second porous layer with the side of the first layer with the conductive lines facing the absorbent core, wherein the at least two conductive lines on the first layer is configured to detect the presence and/or amount of wetness in the absorbent core.

* * * * *